United States Patent
Miller

(10) Patent No.: US 7,192,275 B2
(45) Date of Patent: *Mar. 20, 2007

(54) METHODS FOR CORRECTING DEVIATIONS IN PREPLANNED TOOTH REARRANGEMENTS

(75) Inventor: Ross Miller, Sunnyvale, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/752,193

(22) Filed: Jan. 5, 2004

(65) Prior Publication Data

US 2004/0142299 A1    Jul. 22, 2004

Related U.S. Application Data

(63) Continuation of application No. 10/272,316, filed on Oct. 15, 2002, now Pat. No. 6,761,560, which is a continuation of application No. 09/843,247, filed on Apr. 25, 2001, now Pat. No. 6,488,499.

(60) Provisional application No. 60/199,465, filed on Apr. 25, 2000.

(51) Int. Cl.
    *A61C 3/00* (2006.01)
(52) U.S. Cl. .............................. 433/24; 433/6
(58) Field of Classification Search ............... 433/24, 433/6
    See application file for complete search history.

(56) References Cited

U.S. PATENT DOCUMENTS

| 2,467,432 A | 4/1949 | Kesling |
| 3,660,900 A | 5/1972 | Andrews |
| 3,860,803 A | 1/1975 | Levine |
| 3,916,526 A | 11/1975 | Schudy |
| 3,950,851 A | 4/1976 | Bergersen |
| 3,984,915 A | 10/1976 | Noble et al. |
| 4,014,096 A | 3/1977 | Dellinger |
| 4,195,046 A | 3/1980 | Kesling |
| 4,324,546 A | 4/1982 | Heitlinger et al. |
| 4,348,178 A | 9/1982 | Kurz |
| 4,478,580 A | 10/1984 | Barrut |
| 4,504,225 A | 3/1985 | Yoshii |

(Continued)

FOREIGN PATENT DOCUMENTS

EP    0091876 A1    10/1983

(Continued)

OTHER PUBLICATIONS

Alexander et al., "The DigiGraph Work Station Part 2, Clinical Management," *JCO* (Jul. 1990), pp. 402-407.

(Continued)

*Primary Examiner*—John J Wilson
(74) *Attorney, Agent, or Firm*—Townsend and Townsend and Crew LLP

(57) ABSTRACT

Orthodontic treatment is achieved using a series of successive, removable repositioning appliances, such as thin polymeric shell appliances referred to as aligners. A set of aligners is originally provided to the patient. If the patient's treatment goes off course using the original set of aligners, further aligners are designed and fabricated to move the deviant tooth arrangement back to a target tooth arrangement which was part of the original treatment program.

10 Claims, 3 Drawing Sheets

U.S. PATENT DOCUMENTS

| | | | |
|---|---|---|---|
| 4,505,673 A | 3/1985 | Yoshii | |
| 4,575,805 A | 3/1986 | Moermann et al. | |
| 4,611,288 A | 9/1986 | Duret et al. | |
| 4,656,860 A | 4/1987 | Orthuber et al. | |
| 4,663,720 A | 5/1987 | Duret et al. | |
| 4,742,464 A | 5/1988 | Duret et al. | |
| 4,755,139 A | 7/1988 | Abbatte et al. | |
| 4,763,791 A | 8/1988 | Halverson et al. | |
| 4,793,803 A | 12/1988 | Martz | |
| 4,798,534 A | 1/1989 | Breads | |
| 4,837,732 A | 6/1989 | Brandestini et al. | |
| 4,850,864 A | 7/1989 | Diamond | |
| 4,856,991 A | 8/1989 | Breads et al. | |
| 4,936,862 A | 6/1990 | Walker et al. | |
| 4,937,928 A | 7/1990 | van der Zel | |
| 4,964,770 A | 10/1990 | Steinbichler et al. | |
| 4,975,052 A | 12/1990 | Spencer et al. | |
| 5,011,405 A | 4/1991 | Lemchen | |
| 5,017,133 A | 5/1991 | Miura | |
| 5,027,281 A | 6/1991 | Rekow et al. | |
| 5,035,613 A | 7/1991 | Breads et al. | |
| 5,055,039 A | 10/1991 | Abbatte et al. | |
| 5,059,118 A | 10/1991 | Breads et al. | |
| 5,100,316 A | 3/1992 | Wildman | |
| 5,121,333 A | 6/1992 | Riley et al. | |
| 5,128,870 A | 7/1992 | Erdman et al. | |
| 5,131,843 A | 7/1992 | Hilgers et al. | |
| 5,131,844 A | 7/1992 | Marinaccio et al. | |
| 5,139,419 A | 8/1992 | Andreiko et al. | |
| 5,184,306 A | 2/1993 | Erdman et al. | |
| 5,186,623 A | 2/1993 | Breads et al. | |
| 5,257,203 A | 10/1993 | Riley et al. | |
| 5,273,429 A | 12/1993 | Rekow et al. | |
| 5,278,756 A | 1/1994 | Lemchen et al. | |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,431,562 A | 7/1995 | Andreiko et al. | |
| 5,440,496 A | 8/1995 | Andersson et al. | |
| 5,447,432 A | 9/1995 | Andreiko et al. | |
| 5,452,219 A | 9/1995 | Dehoff et al. | |
| 5,454,717 A | 10/1995 | Andreiko et al. | |
| 5,456,600 A | 10/1995 | Andreiko et al. | |
| 5,474,448 A | 12/1995 | Andreiko et al. | |
| 5,518,397 A | 5/1996 | Andreiko et al. | |
| 5,533,895 A | 7/1996 | Andreiko et al. | |
| 5,542,842 A | 8/1996 | Andreiko et al. | |
| 5,549,476 A | 8/1996 | Stern | |
| 5,587,912 A | 12/1996 | Andersson et al. | |
| 5,605,459 A | 2/1997 | Kuroda et al. | |
| 5,607,305 A | 3/1997 | Andersson et al. | |
| 5,645,421 A | 7/1997 | Slootsky | |
| 5,655,653 A | 8/1997 | Chester | |
| 5,683,243 A | 11/1997 | Andreiko et al. | |
| 5,733,126 A | 3/1998 | Andersson et al. | |
| 5,740,267 A | 4/1998 | Echerer et al. | |
| 5,975,893 A | 11/1999 | Chishti et al. | |
| 6,227,851 B1 * | 5/2001 | Chishti et al. | 433/24 |
| 6,315,553 B1 | 11/2001 | Sachdeva et al. | |
| 6,454,565 B2 | 9/2002 | Phan et al. | |

FOREIGN PATENT DOCUMENTS

| | | |
|---|---|---|
| EP | 0299490 A2 | 1/1989 |
| EP | 0376873 A2 | 7/1990 |
| EP | 0490848 A2 | 6/1992 |
| EP | 0774933 B1 | 5/1997 |
| EP | 0541500 A1 | 6/1998 |
| EP | 0731673 B1 | 9/1998 |
| FR | 2369828 A1 | 6/1978 |
| FR | 2652256 A1 | 3/1991 |
| WO | WO 90/08512 A1 | 8/1990 |
| WO | WO 91/04713 A1 | 4/1991 |
| WO | WO 94/10935 A1 | 5/1994 |
| WO | WO 98/44865 A1 | 10/1998 |
| WO | WO 98/58596 A1 | 12/1998 |

OTHER PUBLICATIONS

Altschuler et al, "Measuring Surfaces Space-Coded by a Laser-Projected Dot Matix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler, "3D Mapping of Maxillo-Facial Prosthesis," AADR Abstract #607,1980, 1 page total.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A Stereophotogrammetric System for the Detection of Prosthesis Loosening in Total Hip Arthroplasty", NATO Symposium on Applications of Human Biostereometrics, Jul. 9-13, 1978, SPIE vol. 166, pp. 112-123.

Baumrind et al., Mapping the Skull in 3-D, Reprinted from The Journal, *California Dental Association*, vol. 48, No. 2 (1972 Fall Issue) 11 pages total.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. pp. 142-166.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized Diagnosis in Orthodontics for Epidemiological Studies: A Progress Report", Abstracts of Papers, *Journal of Dental Research;* vol. 67, Special Issue Mar. 9-13, 1988, p. 128.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized Analysis of Occlusion In The Postcanine Dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Boyd et al., "Three Dimensional Diagnosis and Orthodontic Treatment of Complex Malocclusions With the Invisalign Appliance", *Seminars in Orthodontics*, vol. 7, No. 4 (Dec. 2001), p. 274-293.

Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.

Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.

Burstone (interview), "Dr. Charles J. Burnstone on The Uses of the Computer in Orthodontic Practice (Parts1 and 2)," *Journal of*

*Clinical Orthodontics,* (Part 1) vol. 8, No. 7 , Jul. 1979; (Part 2) vol. 8, No. 8 pp. 539-551, Aug. 1979.

Burstone et al., "Precision Adjustment of the Transpalatal Lingual Arch: Computer Arch Form Predetermination," *Am. Journal of Orthodontics,* vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research,* No. 201 (Dec. 1985), pp. 60-67.

Chiappone, "Constructing the Gnathologic Setup And Positioner" *J. Clin. Orthod.,* 14:121-133, 1980.

Cottingham, "Gnathologic Clear Plastic Positioner" *Am. J. Orthod.,* vol. 55, No. 1, ( Jan. 1969),. pp. 23-31.

Crawford, "Computers in Dentistry: Part 1: CAD/CAM: The Computer Moves Chairside," "Part 2: F. Duret—A Man With A Vision," "Part 3: The Computer Gives New Vision—Literally," "Part 4: Bytes 'N Bites" The Computer Moves From The Front Desk To The Operatory, *Canadian Dental Journal,* vol. 54(9), , (1988), pp. 661-666.

Crawford, "CAD/CAM in the Dental Office: Does It Work?" *Canadian Dental Journal,* vol. 57, No. 2 (Feb. 1991), pp. 121-123.

Crooks, "CAD/CAM Comes to USC," *USC Dentistry,* (Spring 1990) pp. 14-17.

Cureton, "Correcting Mataligned Mandibular Incisors With Removable Retainers" *J. Clin. Orthod.,* 30:390-395, 1996.

Curry et al., "Integrated Three-Dimensional Craniofacial Mapping at the Craniofacial Research Instrumentation Laboratory/University of the Pacific," *Seminars in Orthodontics,* vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery,* vol. 77, No. 6 (Jun. 1986), pp. 877-885.

DCS Dental AG, "The CAD/CAM 'DCS Titan System' for Production of Crown/Bridges" *DSC Production AG,* Jan. 1992, pp. 1-7.

Defranco et al., "Three-Dimensional Large Displacement Analysis of Orthodontic Appliances," *J. Biomechanics,* vol. 9 (1976), pp. 793-801.

Dental Institute University of Zurich Switzerland, Program for International Symposium on Computer Restorations: State of the Art of the CEREC-Method, May 1991, 2 pages total.

DenTrac Corporation, Dentrac document, pp. 4-13.

Duret et al, "CAD-CAM in Dentistry," *Journal of the American Dental Association,* vol. 117 (Nov. 1988), pp. 715-720.

Duret et al., "CAD/CAM Imaging in Dentistry," *Current Opinion in Dentistry,* vol. 1 (1991), pp. 150-154.

Duret, "Vers une prosthese Informatisee," (English translation also attached), *Tonus,* vol. 75, (Nov. 15, 1985), pp. 55-57.

Duret, "The Dental CAD/CAM, General Description of the Project," *Hennson International Product Brochure,* Jan. 1986., 18 pages total.

Economides, "The Microcomputer in the Orthodontic Office," *JCO,* (Nov. 1979), pp. 767-772.

Elsasser, "Some Observations on the History and Uses of the Kesling Positioner" *Am. J. Orthod.,* vol. 36, No. 5, (May 1950) pp. 368-374.

Faber et al., "Computerized interactive orthodontic treatment planning," *Am. J. Orthod.,* vol. 73, No. 1 (Jan. 1978), pp. 36-46.

Felton et al. "A computerized analysis of the shape and stability of mandibular arch form," *Am. Journal of Orthodontics and Dentofacial Orthodpedics,* vol. 92, No. 6 (Dec. 1987), pp. 478-483.

Friede et al., "Accuracy of Cephalometric Prediction in Orthognathic Surgery,"Abstract of Papers, *Journal of Dental Research,* vol. 70 (1987), pp. 754-760.

Gim-Alldent Deutschland, "Das DUX System: Die Technik" 2 pages total.

Grayson, "New Methods for Three Dimensional Analysis of Craniofacial Deformity," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery,* vol. 48, No. 8, Supp. 1, Aug. 1990, p. 5-6.

Guess et al., "Computer Treatment Estimates in Orthodontics and Orthognathic Surgery,"*JCO,* (Apr. 1989), pp. 262-228

Heaven et al., "Computer-based Image Analysis of Artificial Root Surface Caries," Abstracts of Papers, *Journal of Dental Research,* vol. 70,Apr. 17-21, 1991, p. 528.

Hoffmann et al., "Role of Cephalometry for Planning of Jaw Orthopedics and Jaw Surgery Procedures," (Article Summary in English, article in German), *Informationen,* (Mar. 1991), pp. 375-396.

Huckins, "CAD-CAM Generated Mandibular Model Prototype from MRI Data," *AAOMS* 1999, p. 96.

JCO Interviews, "Craig Andreiko, DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The Problem, Electronic Data Transmission and the Law," *AJO-DO,* (Apr. 1988), pp. 478-479.

Jones et al., "An Assessment of the Fit of a Parabolic Curve to Pre- and Post-Treatment Dental Arches," *British Journal of Orthodontics,* vol. 16 (1989), pp. 85-93.

Kamada et al., "Case Reports on Tooth Positioners Using LTV Vinyl Silicone Rubber" J. Nihon University School of Dentistry, 26(1):11-29, 1984.

Kamada et al., "Construction of Tooth Positioners With LTV Vinyl Silicone Rubber and Some Case Reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res. ,* vol. 63, No. 11 (Nov. 1984), pp. 1298-1301.

Kesling, "Coordinating the Predetermined Pattern and Tooth Positioner With Conventional Treatment" *Am. J. Orthod. Oral Surg.,* 32:285-293, 1946.

Kesling, "The Philosophy of the Tooth Positioning Appliance" *Am. J. Orthod. Oral. Surg.,* 31(6):297-304, 1945.

Kleemann et al., "The Speed Positioner" *J. Clin. Orthod.,* 30:673-680, 1996.

Kuroda et al., "Three-dimensional Dental Cast Analyzing System Using Laser Scanning" *Am. J. Orthod. Dentofac. Orthop.,* 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging,* vol. 10, No. 3 (Sep. 1991), pp. 453-461.

Leinfelder et al., "A New Method for Generating Ceramic Restorations: a CAD-CAM System," *Journal Of The American Dental Assoc.,* vol. 118, No. 6 (Jun. 1989), pp. 703-707.

Manetti et al., "Computer-aided Cefalometry and New Mechanics in Orthodontics" (Article Summary in English, article in German), *Fortschr. Kieferorthop.* 44, 370-376 (Nr. 5), 1983.

McCann, Inside the ADA, *Journal Of The American Dental Assoc.,* vol. 118 (Mar. 1989) pp. 286-294.

McNamara et al., "Invisible Retainers", *J. Clinical Orthodontics,* (Aug. 1985) pp. 570-578.

McNamara et al., Chapter 19: Invisible Retainers, *Orthodontic and Orthopedic Treatment in the Mixed Dentition,* Needham Press, Jan. 1993. pp. 347-353.

Moermann et al., "Computer Machined Adhesive Porcelain Inlays: Margin Adaptation after Fatigue Stress," IADR Abstract 339, *Journal of Dental Research,* vol. 66(a) (1987), p. 763.

Mörmann et al., "Marginal Adaptation von adhasiven Porzellaninlays in vitro,"*Schwizerische Monatsschrift fur Zahnmedizin,* vol. 85 (1985), p. 1118-1129.

Nahoum, "The Vacuum Formed Dental Contour Appliance" *The New York State Dental Journal,* 30(9):385-390, Nov. 1964.

Nash, "CEREC CAD/CAM Inlays: Aesthetics and Durability in a Single Appointment," *Dentistry Today,* (Oct. 1990), pp. 20, 22-23, 54.

Nishiyama et al., "A New Construction Of Tooth Repositioner By LTV Vinyl Silicone Rubber" J. Nihon University School of Dentistry, 19(2):93-102, 1977.

Pinkham, "'Foolish' Concept Propels Technology," *Dentist,* Jan./Feb. 1989, 3 pages total.

Pinkham, "Inventor's CAD/CAM May Transform Dentistry," *Dentist*, Sep. 1990, 3 pages total.

Ponitz, "Invisible Retainers", *Am. J. Orthodontics*, vol. 59, No. 3, Mar. 1971, pp. 266-272.

Procera Research Projects, *PROCERA Research Projects* 1993—Abstract Collection, 1993, pp. 3-24.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, "Feasibility of an Automated System for Production of Dental Restorations," PhD Thesis, Univ. of Minnesota, Nov. 1988, 244 pages total.

Richmond et al., Research Reports, "The Development of a 3D Cast Analysis System," *British Journal of Orthodontics*, vol. 13, No. 1, (Jan. 1986) pp. 53-54.

Richmond, "Recording The Dental Cast In Three Dimensions," *Am. J. Orthod. Dentofac. Orthop.*, vol. 92, No. 3, (Sep. 1987), pp. 199-206.

Rudge, "Dental arch analysis: Arch Form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computed Tomography in Maxillofacial Surgical Planning," *Arch Otolamgol Head Neck Surg.* vol. 114 (Apr. 1988), pp. 438-442.

Shilliday, "Minimizing Finishing Problems With the Mini-Positioner" *Am. J. Orthod.* 59:596-599, 1971.

Siemens, "CEREC—Computer-Reconstruction,"High Techn in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden et al., "Three-Dimensional Analysis of Dental Casts by Means of the Optocom," *J. Dent Res*, Jul.-Aug. 1972, vol. 51, No. 4, p. 1101.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Várady et al., Reverse Engineering Of Geometric Models—An Introduction. Computer-Aided Design, 29 (4):255-268, 1997.

Warunek et al., "Clinical Use Of Silicone Elastomer Appliances" *JCO*, MH (10):694-700, 1989.

Warunek et al., "Physical And Mechanical Properties of Elastomers In Orthodontic Positioners" *Am. J. Orthod. Dentofac. Orthop.*, 95:388-400, 1989.

Wells, "Application of the Positioner Appliance in Orthodontic Treatment" *Am. J. Orthodont.*, 58:351-366, 1970.

Williams, "Dentistry and CAD/CAM: Another French Revolution," *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical Measurement of Dental Cast Profile and Application to Analysis of Three-Dimensional Tooth Movement in Orthodontics," *Frontiers in Med. and Biol. Eng'g*, vol. 1, No. 2 (1988), pp. 119-130.

\* cited by examiner

METHODS FOR CORRECTING DEVIATIONS IN PREPLANNED TOOTH REARRANGEMENTS

CROSS-REFERENCES TO RELATED APPLICATIONS

The present application is a continuation of U.S. patent application Ser. No. 10/272,316, filed Oct. 15, 2002 now U.S. Pat. No. 6,761,560, which was a continuation of U.S. patent application Ser. No. 09/843,247, filed Apr. 25, 2001 (now U.S. Pat. No. 6,488,499), which claimed the benefit under 37 CFR §1.78(a)(3) of prior Provisional Application No. 60/199,465, filed on Apr. 25, 2000, the full disclosures of which are incorporated herein by reference.

BACKGROUND OF THE INVENTION

1. Field of the Invention

This invention relates in general to a method of repositioning teeth for use in orthodontic treatment. Particularly, this invention relates to the use of orthodontic appliances for producing tooth movements. More particularly, this invention relates to the use of a plurality of elastic repositioning appliances for producing such tooth movements.

Orthodontic treatments involve repositioning misaligned teeth and improving bite configurations for improved cosmetic appearance and dental function. Repositioning teeth is accomplished by applying controlled forces to the teeth over an extended period of time. This is conventionally accomplished by wearing what are commonly referred to as "braces." Braces comprise a variety of appliances such as brackets, bands, archwires, ligatures, and O-rings. After they are bonded to the teeth, periodic meetings with the orthodontist are required to adjust the braces. This involves installing different archwires having different force-inducing properties or by replacing or tightening existing ligatures. Between meetings, the patient may be required to wear supplementary appliances, such as elastic bands or headgear, to supply additional or extraoral forces.

Although conventional braces are effective, they are often a tedious and time consuming process requiring many visits to the orthodontists office. Moreover, from a patient's perspective, they are unsightly and uncomfortable. Consequently, alternative orthodontic treatments have developed. A particularly promising approach relies on the use of elastic positioning appliances for realigning teeth. Such appliances may comprise a thin shell of elastic material, referred to as an "aligner", that generally conforms to a patient's teeth but is slightly out of alignment with the initial tooth configuration. Placement of an aligner over the teeth applies controlled forces in specific locations to gradually move the teeth into the new configuration. Repetition of this process with successive appliances comprising new configurations eventually move the teeth through a series of intermediate arrangements to a final desired arrangement. A full description of an exemplary elastic polymeric positioning appliance is described in U.S. Pat. No. 5,975,893, and in published PCT application WO 98/58596 which designates the United States and which is assigned to the assignee of the present invention. Both documents are incorporated by reference for all purposes.

Systems of preformed aligners employing technology described in U.S. Pat. No. 5,975,893, are commercially available from Align Technology, Inc., Santa Clara, Calif., under the tradename Invisalign® System. Align Technology, Inc., is the assignee of the present application. The Invisalign® System relies on designing and fabricating at least most of the aligners to be worn by the patient at the outset of treatment. The design of the aligners relies on computer modeling of a series of successive tooth arrangements, and the individual aligners are designed to be worn over the teeth and to elastically reposition the teeth to each of said tooth arrangements. Usually, the set of aligners which is designed and fabricated at the outset of the treatment is able to successfully reposition the teeth to a final desired arrangement. In some cases, however, the treatment deviates from the planned movement stages making continued treatment with the previously provided set of aligners difficult or impossible. Such deviations can arise from biological variations in the individual patient, poor patient compliance, or other factors. The deviations will usually become apparent when the next aligner to be worn in the set of successive aligners does not fit. A poor fit indicates that the tooth arrangement has not progressed to the desired intermediate stage and that the teeth are not ready for the next aligner.

When such deviations occur, the response has usually been to start over with whatever actual tooth arrangement that has been received being the starting point. Aligners are then planned and fabricated to bring the teeth from the actual intermediate arrangement to the desired final arrangement, which is usually the same final arrangement as was the target of the original set of aligners. Starting over, however, can be inefficient and wasteful. Relatively large numbers of aligners can be required, and the remaining aligners in the original set will usually be wasted.

For these reasons, it would be desirable to provide alternative and/or improved methods for making mid-course corrections in orthodontic treatment utilizing sets of aligners or other repositioning appliances which are removable and successively worn by a patient to effect a course of orthodontic treatment. It would be particularly desirable if such methods did not require disposal of all or some of the aligners from the original set and were relatively easy to implement with minimum patient inconvenience. At least some of these objectives will be met by the inventions described hereinafter.

2. Description of the Backpround Art

U.S. Pat. No. 5,975,893, and published PCT application WO98/58596, have been described above. U.S. Pat. No. 6,454,565, relates to the fabrication of orthodontic aligners having varying elastic moduluses. The full disclosures of each of these patents and pending applications are incorporated herein by reference.

BRIEF SUMMARY OF THE INVENTION

According to the present invention, an improved method for repositioning teeth is provided. The method for repositioning generally relies on use of an original set of removable positioning appliances, typically aligners as described in U.S. Pat. No. 5,975,893, the full disclosure of which has been previously incorporated herein by reference. The aligners or other appliances are shaped to move teeth through a plurality of predetermined successive arrangements corresponding to the shape of each appliance. That is, the appliances will be configured to apply repositioning forces to the teeth so that the teeth are moved to an arrangement which closely conforms to the unstressed geometry of the aligner. Thus, after a patient has completed wearing any individual aligner or other appliance, it will be expected that the tooth arrangement will match the shape of the aligner or appliance and that the teeth will be ready to receive a next successive aligner or other appliance. The next successive aligner will be shaped slightly differently from the immediately prior aligner, and it is this difference in shape that will move the teeth still further to their next arrangement. Wearing of successive aligners or other appliances thus can effect an entire course of orthodontic treatment as the teeth are moved through a series of predetermined successive arrangements.

In the case of the Invisalign® System, an original set of aligners will be designed and fabricated at the outset of treatment. The individual aligners will then be available to the patient and/or treating professional so that the aligners may be worn and exchanged as the teeth progress through the expected successive arrangements. Usually, each individual aligner is worn for about two weeks corresponding to one stage of treatment. This period, of course, can vary from several days to several weeks or longer, depending on the individual treatment plan selected for the patient.

The present invention is concerned with those patients who do not progress through treatment as expected and planned. In some cases, an actual tooth arrangement achieved by a patient will differ from the expected tooth arrangement corresponding to the shape of a particular appliance. Such deviation from the expected treatment will usually become apparent when the patient tries to wear the next aligner in a series. If the actual tooth arrangement differs to any significant degree from that which was expected, the next aligner in series will typically not be able to seat properly over the teeth. Such inability to fit or seat on the teeth provides an indication that the actual tooth arrangement which has been achieved at that point in treatment differs from the expected tooth arrangement which should have been achieved after treatment with the immediately prior appliance.

The present invention provides methods for correcting such deviations in the planned and expected treatment path by providing at least one additional removable appliance which has a shape or a compliance selected to move the teeth from the actual (but deviant) tooth arrangement back to one of the predetermined successive tooth arrangements. The tooth arrangement to which the teeth are reconfigured will often be the arrangement to which they should have been at the end of the just completed stage. Alternatively, the arrangement could be any one of the successive stages, usually five stages or fewer beyond the just completed stage, more usually four stages or fewer, and typically no more than three stages beyond the just completed stage.

For the most minor deviations, it will be often be sufficient to provide an aligner or other tooth positioning appliance which has the same geometry as an aligner from the original set, usually as the next aligner in the series. While the aligner will have the same shape, it will be more compliant or elastic so that it can fit and seat over the teeth, even though the shape is further from the geometry of the actual tooth configuration than had been originally intended. The more compliant aligner can then bring the teeth back toward the target configuration for that stage of treatment. Optionally, two or more compliant aligners having the same geometry could be employed, where successive ones of the new aligners will be incrementally stiffer or more rigid to continue to move the teeth toward the target configuration.

The use of additional aligners having the same shape as an original aligner, but which are more compliant, is particularly advantageous since it simplifies design and fabrication of these aligners. The shape or geometry of the aligner would already have been planned during the initial treatment planning process (as described in detail in prior patent U.S. Pat. No. 5,975,893, which has been incorporated herein by reference), and it is necessary only to mold or otherwise fabricate the aligner out of materials having different elasticities. The ability to form aligners having different elasticities is described in detail in co-pending application Ser. No. 09/616,830, related to U.S. Pat. No. 6,454,565, the full disclosures of which have previously been incorporated herein by reference.

In some instances, however, it may not be possible and/or desirable to use aligners having the same geometry as an original aligner to bring the teeth back on to the intended treatment path. In such cases, it will be necessary to design one or more aligners having different shapes in order to move the teeth back from their actual configuration to a tooth arrangement corresponding to one of the appliances from the original set of appliances. Such treatment planning can be performed, for example, by the methods used for the original treatment planning as described in U.S. Pat. No. 5,975,893, the full disclosure of which has been incorporated herein by reference. That is, the actual tooth arrangement, i.e., the tooth arrangement which has been actually achieved in the treatment thus far, will be digitally modeled. Based on the digital model of the actual tooth configuration as a starting point, and a selected one of the target intermediate stages as an ending point, a series of one, two, three, four, or five, or more, new aligners or other positioning appliances can be designed using the computer-aided design protocols described in the patent. Once the new aligner designs are finalized, the digital models of the aligners can be used to fabricate actual aligners using the previously described methods.

The order in which the aligners are to be used will be clearly marked, (e.g., by sequential numbering) so that the patient can place the aligners over his or her teeth at a frequency prescribed by the orthodontist or other treating professional.

For both compliant aligners and differently shaped aligners, the patient will wear the corrective aligners until the teeth have returned to an arrangement which allows an aligner from the original set of aligners to be worn and to move teeth to the next successive arrangement. Depending on the degree of deviation, it may take one, two, three, four, five, or even more, additional aligners or other positioning appliances to provide the desired correction. The corrective aligners or other appliances might be worn from several days to several weeks, or more, until the desired correction is achieved.

DESCRIPTION OF THE SPECIFIC EMBODIMENTS

Figure 1:
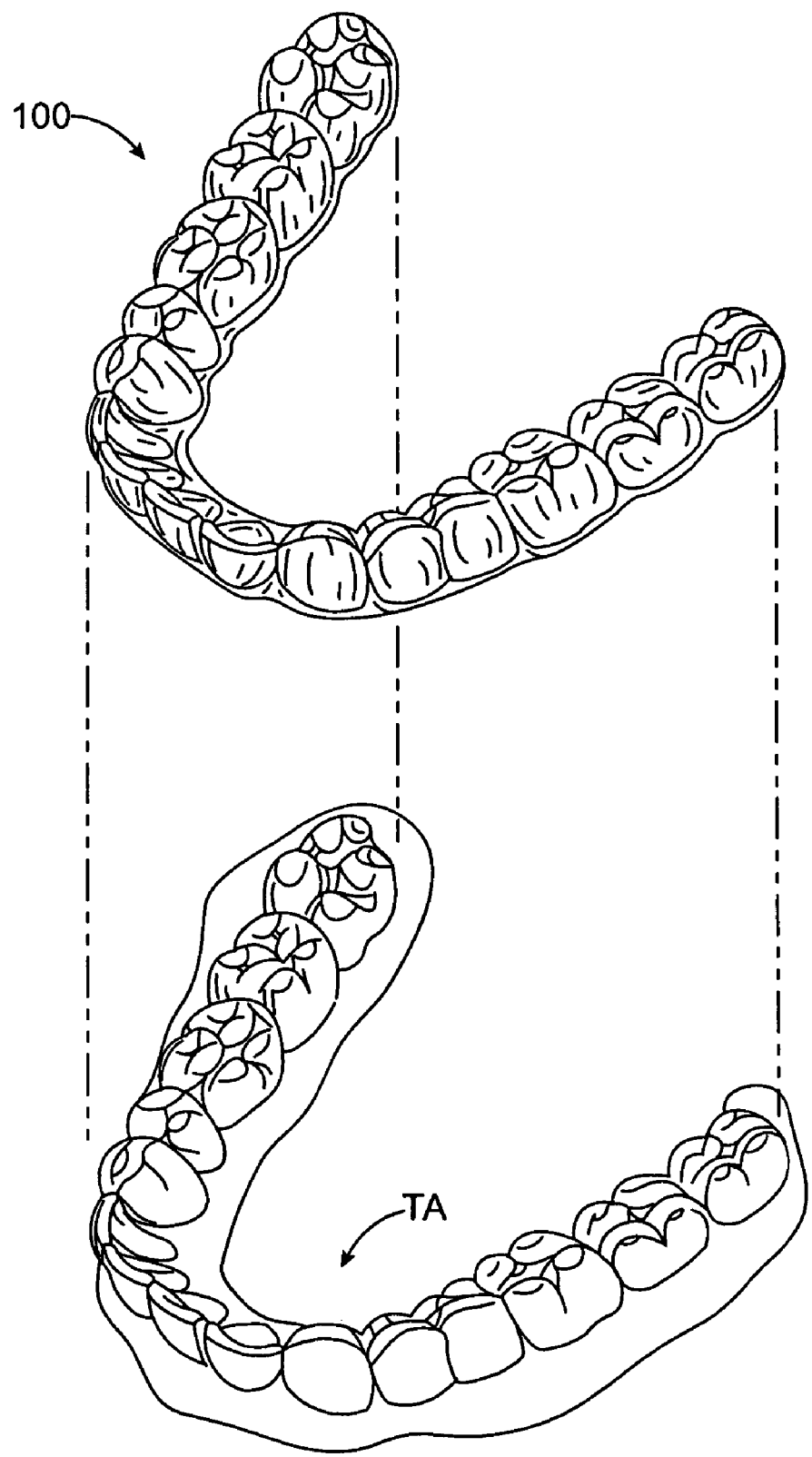
FIG. 1 illustrates an aligner according to the present invention and shows how the aligner is placed over a patient's teeth.

The present invention relies on the use of aligners 100 for positioning teeth in a tooth arrangement TA, as illustrated in FIG. 1. The aligner is a thin shell polymeric appliance of the type commercially available as part of the Invisalign® System available from Align Technology, Inc., Santa Clara, Calif. The planning and fabrication of such aligners is described in detail in issued U.S. Pat. No. 5,975,893, the full disclosure of which has previously been incorporated herein by reference. The aligners 100 are worn by a patient over the tooth arrangement for a sufficient time to rearrange the teeth to a desired subsequent tooth arrangement. A plurality of successive aligners are worn until an entire course of the treatment is completed.

Figure 2:
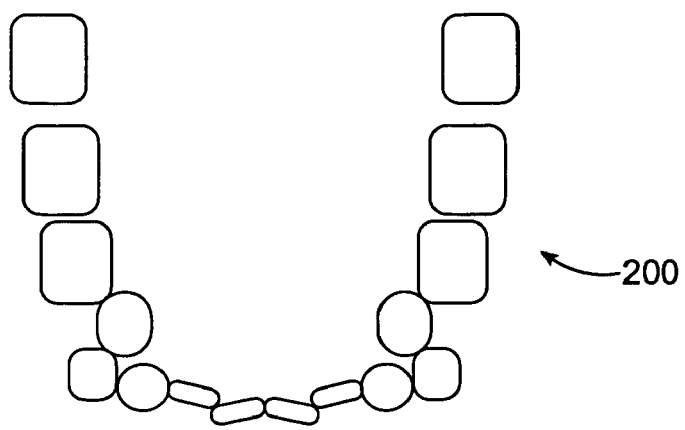
FIGS. 2–4 illustrate an exemplary series of three successive tooth arrangements which may be achieved with the aligners of FIG. 1.
Figure 3:
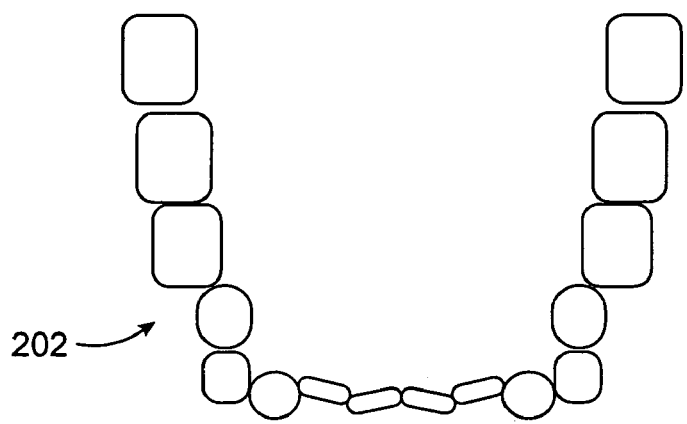
Figure 4:
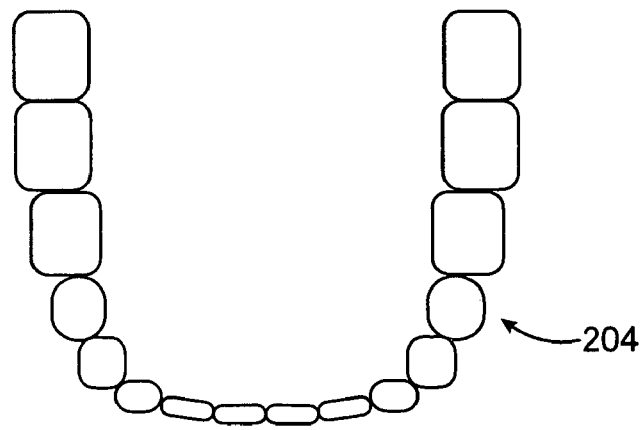

As shown in FIGS. 2–4, multiple stages of treatment will result in the teeth being rearranged. Tooth arrangement 200 shows the teeth in an initial configuration with significant misalignment. Tooth arrangement 202 shows the teeth of arrangement 200 partially reconfigured. Finally, tooth arrangement 204 illustrates the teeth in a desired final configuration. The methods for tooth arrangement of the present invention will typically rely on many more than three stages to achieve a desired reconfiguration. Usually, at least three stages will be required, more usually, at least five stages will be required, and typically 20 or more stages may be utilized.

Figure 5:
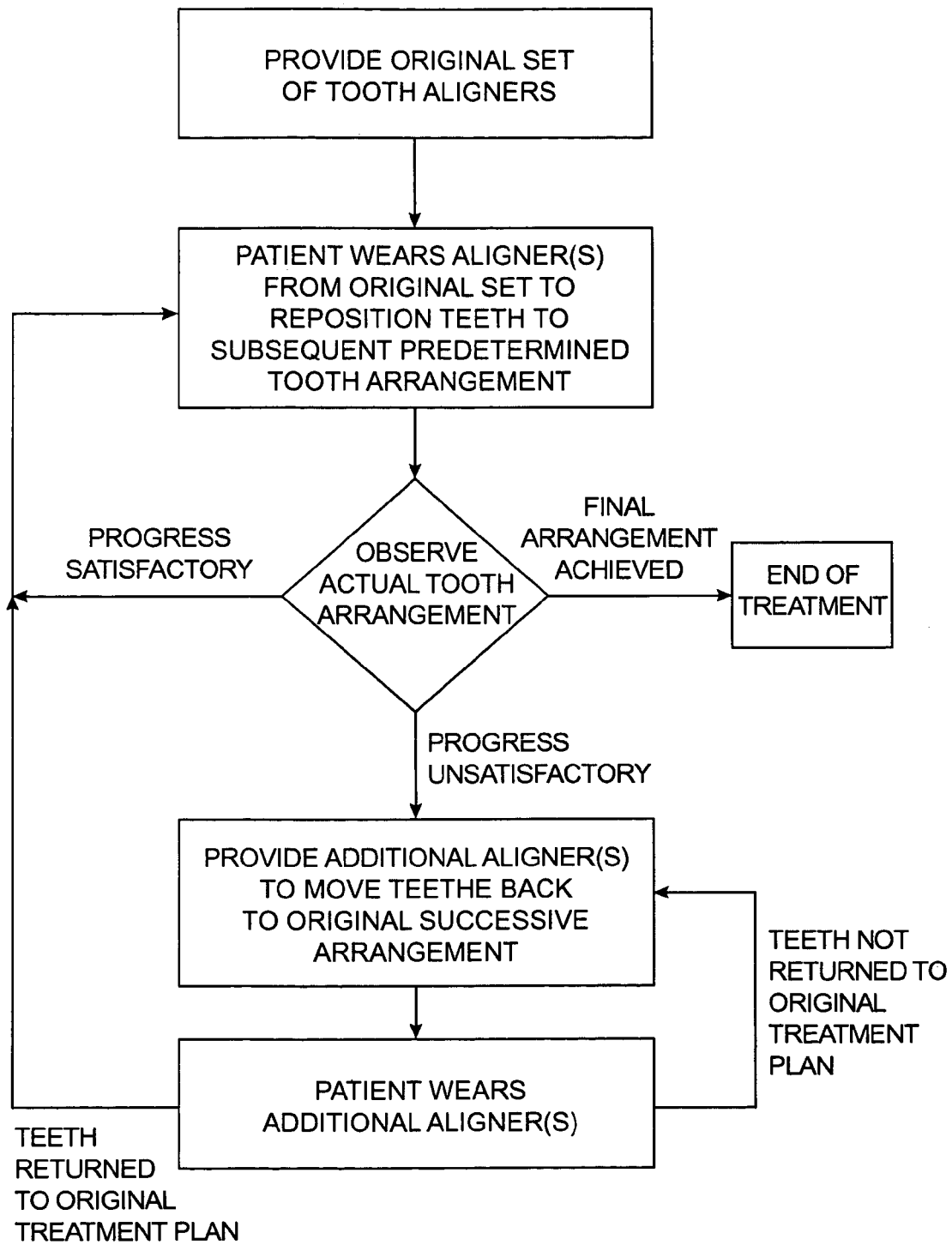
FIG. 5 is a decision tree illustrating an exemplary method according to the present invention.

If at any time during the originally planned course of treatment, the tooth arrangement deviates from a desired intermediate stage, i.e., an intermediate configuration is not achieved, it may be desirable to employ the methods of the present invention to correct such deviation and reconfigure the tooth arrangement to a desired predetermined intermediate stage. As shown in FIG. 5, the patient is initially treated with an original set of tooth aligners. The patient wears individual aligners from the original set to reposition teeth to subsequent predetermined tooth arrangements. Periodically during treatment, the patient or treating professional will observe the actual tooth arrangement achieved at any stage of treatment to see if it is satisfactory. If the progress is satisfactory, the patient will then wear the next aligner in the predetermined set of aligners. The process of confirming satisfactory progress and moving on the next tooth aligner may be repeated until the final desired tooth arrangement is achieved and the treatment ends.

In the case of some patients, however, the progress being achieved will not be satisfactory. For example, the next aligner in the predetermined original set of aligners may not seat or fit properly, indicating that the teeth have not moved to their desired target intermediate arrangement. In such cases, the present invention will provide additional aligner (s) or other reposition appliances to move the teeth back to an arrangement which was part of the original treatment path. The patient will then wear the additional aligner or aligners until the teeth are returned to the original treatment plan. If for any reason the use of the additional aligners is unsatisfactory, it may be appropriate to design and fabricate still further aligners or sets of aligners in order to correct the deviant treatment path. Once the teeth have been returned to an arrangement on the desired treatment path, treatment may then continue with the original aligner set which had been provided to the patient at the outset of treatment.

The aligners will be marked in some manner, typically by sequential numbering directly on the aligners or on tags, pouches, or other items which are affixed to or which enclose each aligner, to indicate their order of use. Optionally, written instructions may accompany the system which set forth that the patient is to wear the individual aligners in the order marked on the aligners or elsewhere in the packaging.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for orthodontic treatment comprising:
   providing an original set of thin polymeric shell orthodontic aligners to a patient, wherein each aligner in the set was shaped to move teeth through a plurality of planned successive tooth arrangements, and wherein the shape of each aligner in the original set corresponds to one of the planned successive tooth arrangements;
   observing whether a particular thin polymeric shell orthodontic aligner fits over the teeth at a corresponding tooth arrangement in order to determine if the actual arrangement of the teeth deviates from the corresponding planned tooth arrangement; and
   if the actual tooth arrangement deviates from the planned tooth arrangement, providing at least one additional polymeric shell orthodontic aligner which is shaped to move the teeth from their actual arrangement back to one of the originally planned successive tooth arrangements so that at least one of the original set of aligners may be used, wherein the patient uses both the at least one additional aligner and one or more of the original set of aligners to complete the orthodontic treatment.

2. A method as in claim 1, wherein the at least one additional polymeric shell aligner is shaped the same as an appliance in the original set hut has a different compliance selected to move the teeth from an actual deviant tooth arrangement to a designed tooth arrangement.

3. A method as in claim 1, wherein providing the original set of aligners comprises providing a series of at least two aligners.

4. A method as in claim 3, wherein the at least two aligners arc marked to indicate their order of use.

5. A method as in claim 1, wherein providing the original set of aligners comprises providing a series of at least three aligners.

6. A method as in claim 5, wherein the at least three aligners are marked to indicate order of use.

7. A method as in claim 1, wherein providing the original set of aligners comprises providing a series of at least four aligners.

8. A method as in claim 7, wherein the at least four aligners are marked to indicate order of use.

9. A method as in claim 1, wherein providing the original set of aligners comprises providing a series of at least five aligners.

10. A method as in claim 9, wherein the at least five aligners are marked to indicate order of use.

* * * * *